United States Patent
Tobias et al.

(10) Patent No.: US 9,079,049 B2
(45) Date of Patent: Jul. 14, 2015

(54) RESPIRATORS WITH A SACRIFICIAL CARTRIDGE FOR END OF SERVICE LIFE INDICATION

(75) Inventors: Peter Tobias, Minneapolis, MN (US); Lynn Feiner, Warwick, RI (US)

(73) Assignee: Honeywell International Inc., Morristown, NJ (US)

( * ) Notice: Subject to any disclaimer, the term of this patent is extended or adjusted under 35 U.S.C. 154(b) by 404 days.

(21) Appl. No.: 13/287,836

(22) Filed: Nov. 2, 2011

(65) Prior Publication Data

US 2013/0104900 A1     May 2, 2013

(51) Int. Cl.
| | |
|---|---|
| A62B 7/10 | (2006.01) |
| A62B 19/00 | (2006.01) |
| A62B 23/02 | (2006.01) |
| A62B 9/00 | (2006.01) |
| A61M 16/10 | (2006.01) |
| A62B 18/08 | (2006.01) |

(52) U.S. Cl.
CPC .............. *A62B 9/006* (2013.01); *A61M 16/105* (2013.01); *A61M 16/107* (2014.02); *A62B 18/088* (2013.01); *A62B 19/00* (2013.01)

(58) Field of Classification Search
CPC ...... A62B 18/088; A62B 9/006; A62B 19/00; B01D 46/442; B01D 46/0086; B01D 53/0454; A61M 16/105; A61M 16/107; A61M 16/06; A61M 2205/125
USPC ............. 128/202.22, 204.16, 205.23, 205.27, 128/205.29, 206.12, 206.15, 206.17; 73/31.01, 31.02; 55/DIG. 34, DIG. 35; 96/117, 397, 399, 417, 96, 111; 95/8, 95/11, 12
See application file for complete search history.

(56) References Cited

U.S. PATENT DOCUMENTS

| | | | |
|---|---|---|---|
| 3,819,282 A | 6/1974 | Schultz | |
| 4,512,191 A | 4/1985 | Sexton | |
| 4,873,970 A | 10/1989 | Freidank et al. | |
| 5,003,985 A | 4/1991 | White et al. | |
| 5,413,097 A | * 5/1995 | Birenheide et al. | ...... 128/206.17 |
| 5,659,296 A | 8/1997 | Debe et al. | |
| 5,950,621 A | 9/1999 | Klockseth et al. | |
| 6,040,777 A | 3/2000 | Ammann et al. | |

(Continued)

FOREIGN PATENT DOCUMENTS

| | | |
|---|---|---|
| DE | 19543056 A1 | 5/2007 |
| WO | 2009029326 A1 | 3/2009 |
| WO | 2009029426 A1 | 3/2009 |

OTHER PUBLICATIONS

PCT/US2012/062360, PCT International Search Report, dated Jan. 21, 2014, 5 pages.

(Continued)

*Primary Examiner* — Justine Yu
*Assistant Examiner* — Douglas Sul
(74) *Attorney, Agent, or Firm* — Conley Rose, P.C.; Kristin Jordan Harkins (57) ABSTRACT

A respirator service life indication system may include a breathing apparatus having an air purifying element; and a service life indicator arranged in a parallel flow configuration with the breathing apparatus. The service life indicator typically might have a sacrificial cartridge, and a sensor disposed downstream of the sacrificial cartridge and configured to detect a contaminant concentration above a predetermined threshold in a gas stream passing through the sacrificial cartridge.

20 Claims, 3 Drawing Sheets

(56) References Cited

U.S. PATENT DOCUMENTS

| | | | |
|---|---|---|---|
| 6,187,596 B1 * | 2/2001 | Dallas et al. | 436/169 |
| 7,042,346 B2 | 5/2006 | Paulsen | |
| 7,148,806 B2 | 12/2006 | Anttila et al. | |
| 7,201,036 B2 * | 4/2007 | Custer et al. | 73/31.02 |
| 7,442,237 B1 * | 10/2008 | Gardner | 96/117.5 |
| 7,537,648 B1 | 5/2009 | Karwacki et al. | |
| 7,625,760 B2 | 12/2009 | Kitaguchi et al. | |
| 7,638,042 B2 | 12/2009 | Astle et al. | |
| 7,703,455 B2 | 4/2010 | Bunke et al. | |
| 7,736,495 B2 | 6/2010 | Ikeyama et al. | |
| 7,761,188 B2 | 7/2010 | Palmerton et al. | |
| 2005/0188749 A1 | 9/2005 | Custer et al. | |
| 2007/0240719 A1 * | 10/2007 | Duarte | 128/205.27 |
| 2007/0277592 A1 | 12/2007 | Johansson et al. | |
| 2009/0288561 A1 | 11/2009 | Palmerton et al. | |
| 2010/0017148 A1 | 1/2010 | Bos et al. | |
| 2010/0153023 A1 * | 6/2010 | Parham et al. | 702/34 |
| 2012/0085349 A1 | 4/2012 | Tobias et al. | |
| 2013/0047982 A1 | 2/2013 | Tobias et al. | |
| 2013/0239813 A1 * | 9/2013 | Rakow et al. | 96/108 |

OTHER PUBLICATIONS

PCT/US2012/062360, PCT Written Opinion of the International Searching Authority, Jan. 21, 2014, 6 pages.

PCT/US2014/033123, PCT International Search Report, dated Aug. 1, 2014, 3 pages.

PCT/US2014/033123, PCT Written Opinion of the International Searching Authority, Aug. 1, 2014, 6 pages.

* cited by examiner

RESPIRATORS WITH A SACRIFICIAL CARTRIDGE FOR END OF SERVICE LIFE INDICATION

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Powered air-purifying respirators (PAPRs) utilize a powered mechanism (e.g., an electric blower) to draw ambient air through an air-purifying element to remove one or more contaminants from the ambient air. PAPRs are generally designed to provide respiratory protection against atmospheres with solid/liquid contaminants (e.g., dusts, mists, etc.), vapors and/or gases above certain safety levels by reducing the contaminant levels below certain safety criteria. For example, the safety criteria can specify that the concentrations should not be immediately dangerous to life or health and that the atmosphere contains adequate oxygen to support life. The air-purifying elements are generally used for a predetermined period of time and then discarded to avoid a potential breakthrough of a contaminant, which results in the disposal of an air-purifying element having significant remaining capacity.

SUMMARY

In an embodiment, a respirator service life indication system comprises a breathing apparatus comprising an air purifying element; and a service life indicator arranged in a parallel flow configuration with the breathing apparatus. The service life indicator comprises a sacrificial cartridge, and a sensor disposed downstream of the sacrificial cartridge and configured to detect a contaminant concentration above a predetermined threshold in a gas stream passing through the sacrificial cartridge.

In an embodiment, a powered air-purifying respirator service life indication system comprises a powered air-purifying respirator, a service life indicator, and an indicator device configured to present an indication from the sensor in response to the detection of a contaminant concentration above a predetermined threshold in the second air stream. The power air-purifying respirator comprises one or more air purifying elements, and a blower assembly configured to draw a first air stream from an ambient environment, pass the first air stream through the one or more air purifying elements, and pass the first air stream to a mask. The service life indicator comprises a sacrificial cartridge, a sensor disposed downstream of the sacrificial cartridge, and a secondary blower assembly configured to draw a second air stream from the ambient environment, pass the second air stream through the sacrificial cartridge and past the sensor, and pass the second air stream back to the ambient environment.

In an embodiment, a method comprises purifying a first air stream using a breathing apparatus comprising an air purifying element to produce a purified first stream; supplying the purified first air stream to a user; passing a second air stream through a sacrificial cartridge to produce a third stream; exhausting the third stream to an ambient environment; and detecting a contaminant concentration above a predetermined threshold in the third stream.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Disclosed herein is a service life indicator for use with a breathing apparatus comprising one or more air-purifying elements. The use of the service life indicator as described herein may represent a cost effective and relatively accurate means for determining when an air purifying media should be replaced. Since the service life indicator may be used to determine the end-of-life status of an air purifying element, the service life indicator may also be referred to as an end-of-service life indicator (ESLI). As described below, the ESLI is arranged in parallel with a flow path through a breathing apparatus so that the ESLI has a separate inlet and outlet from the inlet and outlet of the breathing apparatus. A sacrificial cartridge containing an air purifying media similar to that of the air purifying media used in the breathing apparatus may be used in combination with a sensor to detect a breakthrough of one or more contaminants, thereby indicating the need for a replacement of the air purifying media in the breathing apparatus. This configuration may provide an actual indicator of the end of the service life of the air purifying media rather than basing the replacement schedule simply on the time in service. Further, the use of the parallel configuration helps prevent any contaminant breakthrough from the sacrificial cartridge from affecting the user of the breathing apparatus.

Figure 1:
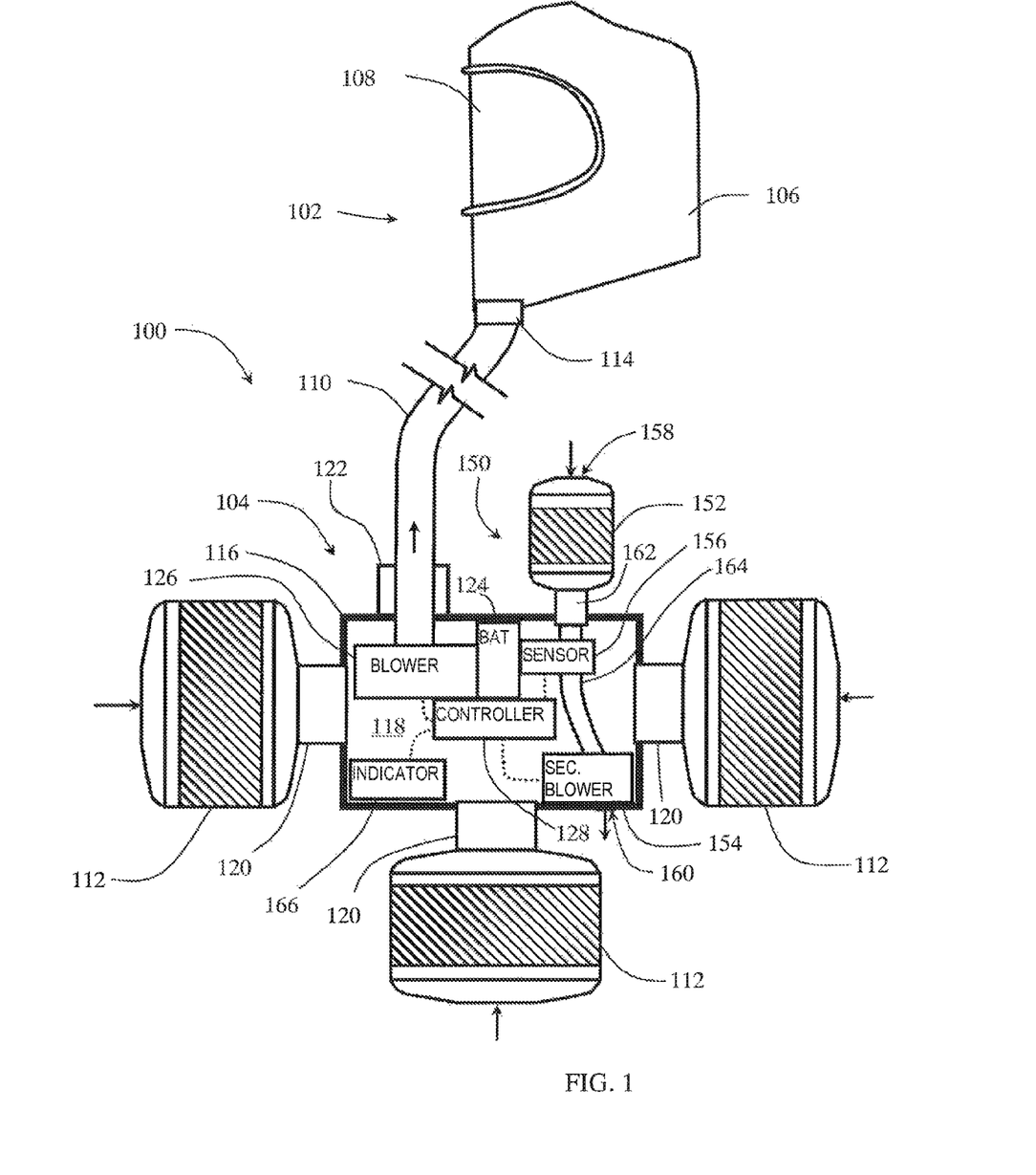
FIG. 1 schematically illustrates a breathing apparatus and service life indicator according to an embodiment.

FIG. 1 is a schematic illustration of an embodiment of a breathing apparatus 100 and ESLI 150 that may be used to supply purified air through one or more air purifying elements to a user. The breathing apparatus 100 includes a face mask 102, a housing assembly 104 comprising one or more air-purifying elements 112, and a fluid connection apparatus 110 extending between mask 102 and housing assembly 104. The ESLI 150 includes one or more sacrificial cartridges 152, a secondary pump or blower 154, and a sensor 156 for detecting the breakthrough of one or more contaminants from the one or more sacrificial cartridges 152.

The mask 102 may generally include a mask body 106, a transparent face shield or window 108, a seal, and a fastening harness. The seal may extend around a periphery of the mask body 106 to form a sealing engagement with the face of a user, thereby preventing contaminants and untreated air from entering the mask 102. In an embodiment, the mask 102 is continuously pressurized by the flow of purified air supplied from the housing assembly 104 to allow air to exit the mask and prevent any contaminated air outside the mask 102 from entering the mask 102. The mask body 106 may be fabricated from an elastomeric material including, but not limited to, a rubber and/or a silicone/organic rubber blend material to enable the mask 102 to conform to the face of the user. The mask body 106 may be shaped so that the mask 102 fits over the face of the user, and an interior chamber may be defined between the body 106, the face shield 108, and the face of the user. The mask 102 may be sized to substantially enclose the nose, mouth, and eyes of the user such that an airtight engagement is created between the seal and the face of the user. In some embodiments, the mask 102 may be sized to substantially cover only the nose and mouth of the user, or in some embodiments, the entire head of the user. When present, an optional fastening harness may maintain a substantially airtight engagement between the user's face and the mask 102. The harness may be adapted to engage the user's head at various positions to allow for a secure engagement during use.

The mask 102 may comprise an inlet 114 that enables a first end of the fluid connection apparatus 110 to be securely coupled to mask 102 for delivery of purified air to the mask 102. In an embodiment, the mask 102 may be formed with more than one inlet 114 depending on the application and environment in which the mask 102 is used. For example, the mask 102 may include an inlet that enables the mask 102 to be coupled to a pressurized air tank and/or the housing assembly 104. The mask 102 may also be formed with an exhaust assembly that enables exhaust airflow to exit the mask 102 (e.g., during exhalation of the user).

The housing assembly 104 may include a housing 116 that is formed as an integral, single unit and defines an enclosure 118 therein. In an embodiment, the housing assembly 104 may comprise a plurality of housing members coupled together to form an enclosure therein. The housing assembly 104 may generally be sized so that the housing assembly 104 is portable and may be carried by the user. For example, the housing assembly 104 may be carried around a user's waist via a belt, on their back, or over their shoulder using a shoulder strap, harness, or any other suitable carrying apparatus.

The housing assembly 104 comprises one or more inlet ports 120 with one or more corresponding air purifying elements 112 coupled thereto and at least one exhaust port 122. The housing assembly 104 is substantially sealed so that the inlet ports 120 provide the only means for air to enter housing assembly 104 prior to being supplied to the user for breathing. A second end of the fluid connection apparatus 110 is coupled to exhaust port 122 to provide fluid communication between the housing assembly 104 and the mask 102 for use by the user.

Air entering ports 120 through the air purifying elements 112 passes to the housing assembly 104 prior to being exhausted through the exhaust port 122 towards the user. The housing assembly 104 comprises a power source 124 (e.g., a battery assembly), a controller 128, and a blower assembly 126. Each component is described in more detail below. In an embodiment, the power source 124, the controller 128, and/or blower assembly 126 can be coupled to the housing assembly 104 independently of the remaining components. For example, the power source 124 may be external to the housing assembly 104 and coupled thereto by an electrical connector. The housing assembly 104 may provide the primary support structure for the components housed therein, the inlet ports 120 coupled to the air purifying elements 112, and the exhaust port 122.

Each inlet port 120 may be substantially cylindrical and comprise a connection mechanism to enable an air purifying element 112 to be removably or fixedly coupled to the inlet port 120. A variety of different mechanisms or means may be used to removably attach one or more air purifying elements 112 to the inlet port 120. Suitable connection mechanisms for coupling the air purifying element 112 to an inlet port include, but are not limited to, screws, fasteners, clips, latches and the like. Other suitable connection mechanisms include snap-fit filter cartridges and corresponding threaded connections on the air purifying element 112 and the inlet port 120. In some embodiments, various inlet shapes and configurations are possible, such as a T-shaped inlet or a Y-shaped inlet, which may accommodate multiple air purifying elements 112 per inlet port 120.

In the embodiment illustrated in FIG. 1, three inlet ports 120 are provided with a corresponding air purifying element 112 coupled to each inlet port 120. Each inlet port 120 may be of a standard size and the connection means may permit various accessories, including but not limited to the air purifying elements 112, cover plates, and/or intake devices to be coupled thereto. In an embodiment, the connection means may comprise a valve or seal to substantially seal the inlet port when the air purifying element 112 is not coupled thereto. This may allow the air purifying element 112 to be disconnected from the inlet port 120 during use and replaced without allowing any contaminated, unpurified air to pass into to the housing assembly 104 or the downstream mask 102 and affect the user. As will be apparent to one of ordinary skill in the art with the benefit of this disclosure, the housing assembly 104 may comprise more or less than three inlet ports 120. In an embodiment, the housing assembly 104 may comprise one, two, three, four, five, six, seven, eight, or more inlet ports 120 each coupled to one or more air purifying elements 112. Further, the orientation, relative location, and/or overall size and shape of inlet ports 120 may be different than those illustrated.

The air purifying elements 112 may be removably coupled to each inlet port 120. As used herein, the term "air purifying element" refers to any device used to adsorb, absorb, filter, and/or or detoxify (e.g., destroy, inactivate, and/or render harmless) airborne contaminants, poisons, irritants, particulates, or the like to a predetermined threshold, regardless of the physical configuration, shape, or design of such device. The term "purify" when used with the term "air purifying element" and/or the removal of a contaminant from an air stream does not require the absolute removal of all contaminants, but rather implies the reduction of at least one contaminate to a predetermined level. In an embodiment, the air purifying elements may comprise filter canisters that may be removably coupled to the inlet ports 120, though various designs such as fixed or removable canisters, cartridges, and/or patches may also be used. In an embodiment, the air purifying elements 112 may be passive elements that are designed to adsorb, absorb, and/or filter contaminants from the air being introduced to the housing assembly 104 through the air purifying elements 112. For example, in an embodiment, air purifying elements 112 may use fiber filters to filter particulate contaminants and/or granulated charcoal or other similar adsorption materials to facilitate preventing chemical contaminants from entering the housing assembly 104.

The particular type of air purifying elements 112 used will dependent, at least in part, on the environment in which they are to be used. In general, the air purifying elements 112 may remove at least a portion of any contaminants including, but not limited to, particulate matter, gaseous contaminants, and/or biological contaminants and may comprise a variety of filtering, adsorption, absorption, and/or detoxifying materials according to the intended operating environment.

In an embodiment, at least a portion of the air purifying element 112 may be used to remove one or more particulate matter components from the air entering the inlet 120 through the air purifying element 112. Particulate matter may include various solid particles, liquid droplets, and/or organic contaminants (e.g., bacteria, viruses, and the like) generally smaller than about 1 mm, about 100 micrometers, about 10 micrometers, or about 1 micrometer in diameter (e.g., aerodynamic diameter). Particular matter may be removed by a variety of purifying media, and in an embodiment, the air purifying element 112 may comprise a high efficiency particulate air (HEPA) filter, an ultra-low penetration air filter (ULPA), or the like.

In an embodiment, at least a portion of the air purifying element 112 may be used to remove one or more vapors and/or gaseous contaminants from the air entering the inlet 120 through the air purifying element 112. The vapors and/or gaseous contaminants may comprise organic and/or inorganic compounds. Various organic compounds may include the class of compounds referred to as volatile organic compounds (VOCs) such as those recognized by the Occupational Safety and Health Administration (OSHA), the National Institute for Occupational Safety and Health (NIOSH), and various other regulatory agencies. Representative organic compounds may include, but are not limited to, substituted or unsubstituted carbon compounds including alkanes, cycloalkanes, aromatic compounds, aliphatic compounds alicyclic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, acetonitrile, formaldehyde and combinations thereof. The vapors and/or gaseous contaminants may also comprise inorganic compounds, including but not limited to, ammonia, mercury vapor, halogenated compounds, and the like.

A variety of purifying media may be used to remove one or more vapors and/or gaseous contaminants from the air entering the inlet 120 through the air purifying element 112. In an embodiment, the purifying media comprises a sorbent media capable of sorbing (e.g., adsorbing and/or absorbing) vapors and/or gases of interest expected to be present under the intended use conditions. The sorbent media may be sufficiently porous to permit the flow of air or other gases therethrough, and may be in the form of a finely-divided solid (e.g., powder, beads, flakes, granules, and/or agglomerates) and/or a porous solid (e.g., an open-celled foam). The sorbent media may be of any type known to be suitable for removing gases and vapors from fluids, such as air, to be inhaled through a respirator. Suitable sorbent media materials may include, but are not limited to, ion exchange resins, activated carbon, impregnated carbon, alumina and other metal oxides that can remove a vapor of interest by adsorption, treated clays and other minerals comprising acidic solutions such as acetic acid or alkaline solutions such as aqueous sodium hydroxide, molecular sieves (e.g., various zeolites), other inorganic sorbents (e.g., silica), various organic sorbents, metal-organic frameworks (MOFs), and any combinations thereof. Combinations of sorbent media can be provided in a mixed configuration and/or in a layered configuration to form mixtures and/or purifying layers.

The sorbent media particle size can vary depending, at least in part, on the form of the air purifying media, the desired flow rate, and/or the desired sorbent media capacity. In an embodiment, sorbent media may comprise particles having sizes ranging from about 4 to about 3,000 micrometers average diameter, or from about 30 to about 1,500 micrometers average diameter. Mixtures of sorbent media particles having different size ranges may also be employed. Various configurations for retaining the sorbent media within the air purifying element 112 are known and may include the use of support plates, various binders, retaining materials, and the like.

The blower assembly 126 is coupled in fluid communication with the one or more inlet ports 120 and the fluid connection apparatus 110 to facilitate maintaining a positive pressure air flow to mask 102. The blower assembly 126 may be configured to provide the user with a predetermined air flow, at an approximately constant flow rate, to maintain a positive pressure within mask 102. The predetermined air flow rate may be based on the anticipated need of the user and may vary depending on the type of anticipated activity. In an embodiment, the blower assembly 126 may be electronically-controlled (e.g., by the controller 128). The blower assembly generally comprises a blower and a motor to drive the blower. The blower assembly 126 may comprise any type of blower including, but not limited to, a centrifugal fan, a low profile fan, impeller, rotary air pump, or the like.

The blower assembly 126 and the controller 128 are powered by the power source 124. The power source 124 may comprise a source of electrical power and may include a battery assembly and/or a power supply coupled to an external source of electrical power. The use of a battery assembly may provide for a portable system that provides a low voltage direct current to the components of the breathing apparatus 100 and/or the ESLI 150. Alternatively, the power source 124 may comprise an inverter coupled to a battery assembly to allow the components to be powered by alternating current. In an embodiment, a battery assembly may comprise a plurality of rechargeable batteries such as nickel metal hydride (NiMH) batteries, nickel-cadmium (NiCd) batteries, lithium ion batteries. Additional suitable batteries may include, but are not limited to, metal acid batteries, sulfur dioxide lithium (LiSO2) batteries, and lithium CR123 batteries. In addition, the battery assembly may comprise non-rechargeable, disposable batteries. In an embodiment, the housing assembly 104 may comprise an electrical coupling to enable the batteries to be recharged through a connection to an external power source such as a standard 110 volt AC power source, a battery charger, and/or through an automobile power receptacle.

Operation of the breathing apparatus 100 may be controlled by the controller 128. The controller 128 may comprise one or more processors, various circuits, and electrical couplings to the controlled components to facilitate control of the power source 124, the blower assembly 126, and optionally the ESLI 150. In an embodiment, the controller 128 may be electrically coupled to a plurality of optional sensors mounted within housing assembly 104 including, but not limited to, a pressure sensor to detect a low air flow or leak, a voltage sensor to determine proper operation of the electrical components, and/or a battery sensor to determine the battery level. The controller 128 may comprise a power switch to initiate operation of the breathing apparatus 100. An optional user interface or indicator device 166 may also be used to allow a user to provide inputs (e.g., setting the predetermined thresholds, the air flow rate, etc.), control various operations of the breathing apparatus 100 and/or the ESLI 150, and/or receive and/or display various outputs from the controller 128 (e.g., battery levels, sensor outputs, etc.). For example, the user interface or indicator device 166 may present an indication such as an audible, visual, and/or tactile alarm on the indicator device 166 when a breakthrough of the sacrificial cartridge 152 is detected by the sensor 156.

In an embodiment, a memory for storing one or more control programs and/or sensor outputs may be associated with the controller 128. The memory may be comprised of RAM and/or one or more disk drives, solid state memory devices, and/or optical memory devices. The memory may be used for non-volatile storage of data (e.g., the outputs of one or more sensors), and the memory may be used to store programs operable to control and operate the breathing apparatus 100, the ESLI 150, and their respective components. The memory may be referred to in some contexts as computer readable storage media and/or non-transitory computer readable media.

In an embodiment, the controller 128 may be coupled to a speed sensor to monitor the speed of the blower in the blower assembly 126 and control the speed of the motor driving the blower in response to the monitored blower speed. The controller 128 may then be used to ensure that the flow rate of air through the breathing apparatus 100 is at or about a predetermined flow rate. In an embodiment, the controller 128 is connected to the speed sensor that senses that rotational speed of the shaft of the blower, compares the sensed speed to a predetermined speed set in the controller 128, and adjusts the power to the motor so that the sensed speed matches the predetermined speed. The controller 128 may comprise a look-up table or correlation equation or table to correlate the motor speed to a flow rate through the blower assembly 126. To allow this type of control, the controller 128 may have a power supply circuit that is connected to the power source 124 and the motor to control the current supplied to the motor.

During operation of the breathing apparatus 100, air is drawn into the one or more air purifying elements 112 and through the inlet ports 120. The air purifying elements 112 remove one or more contaminants from the air as it passes through the air purifying elements 112 and into the enclosure 118 within the housing assembly 104. The air is then pumped via the blower assembly 126 through the exhaust port 122 and the fluid connection apparatus 110 towards the mask 102 for inhalation by the user. The air purifying elements 112 may be exchanged during operation and/or when the breathing apparatus 100 is not in use without compromising the safety of the user.

In addition to the breathing apparatus 100, the ESLI 150 may also operate during the operation of the breathing apparatus 100 in order to provide an indication when the air purifying elements 112 should be exchanged or replaced. The ESLI 150 comprises an ESLI inlet 162 with a corresponding sacrificial cartridge 152 coupled thereto. The ESLI inlet 162 is coupled to a flow apparatus 164 having an ESLI outlet 160 that discharges the air entering the ESLI inlet 162 to the ambient atmosphere surrounding the ESLI 150. The flow apparatus 164 is substantially scaled so that air entering the ESLI inlet 162 passes out of the ESLI outlet 160. The ESLI 150 flow configuration may be referred to as a parallel configuration with respect to the breathing apparatus 100 based on the separate inlets and outlets associated with the breathing apparatus 100 and the ESLI 150. In other words, the air entering the ESLI inlet 162 is exhausted to the ambient environment and does not contact or mix with the air passing through the breathing apparatus 100. The sensor 156 is coupled to the flow apparatus 164, the secondary blower, and/or the ESLI outlet 160 downstream of the sacrificial cartridge 152 and disposed in contact with the air that has passed through the sacrificial cartridge 152. A secondary blower assembly 154 may be coupled to the flow apparatus 164 to provide the air flow through the ESLI 150, as described in more detail below.

The ESLI inlet 162 may be substantially cylindrical and comprise a connection means to enable the sacrificial cartridge 152 to be removably or fixedly coupled to the ESLI inlet 162. As discussed above with respect to the inlet ports 120 on the breathing apparatus 100, various mechanisms or means may be used to removably attach the sacrificial cartridge 152 to the ESLI inlet 162. Suitable connection mechanisms for coupling the sacrificial cartridge 152 to ESLI inlet 162 include, but are not limited to, screws, fasteners, clips, latches and the like. Other suitable connection mechanisms include snap-fit filter cartridges and corresponding threaded connections on the sacrificial cartridge 152 and the ESLI inlet 162. The connection mechanism associated with the sacrificial cartridge 152 may be different and/or differently sized than the connection mechanisms associated with the inlet port 120 and the air purifying elements 112. Since the sacrificial cartridge 152 may have a smaller air purifying capacity than the air purifying element 112, the different and/or differently sized connection mechanisms may prevent the sacrificial cartridge 152 from inadvertently be coupled to an inlet port 120 or an air purifying element 112 inadvertently being coupled to the ESLI inlet 162. In some embodiments, various inlet shapes and configurations are possible, such as a T-shaped inlet or a Y-shaped inlet, which may accommodate multiple sacrificial cartridges 152.

The ESLI 150 is intended to sample the same or similar ambient fluids (e.g., the ambient air) as the breathing apparatus 100, and the ESLI inlet 158 may be located in proximity to the inlets of the air purifying elements 112. In an embodiment, the ESLI inlet 162 may be located within about 10 feet, about 8 feet, about 6 feet, about 4 feet, about 2 feet, or about 1 foot of the inlets to the air purifying elements 112 to allow the ESLI 150 to sample the same fluids as the breathing apparatus 100.

The sacrificial cartridge 152 is selected to provide an indication of the useful capacity of the air purifying elements 112 associated with the breathing apparatus 100. In an embodiment, the "useful capacity" of the air purifying elements 112 may be less than the total capacity of the air purifying elements 112 to take into account various factors such as safety factors. The sacrificial cartridge 152 may be smaller than the air purifying elements 112 in size, the amount of air purifying media contained therein, and purifying capacity. As described in more detail herein, the air flow rate through the ESLI 150 may be controllably reduced relative to the airflow through the breathing apparatus 100, which when combined with the reduced size of the sacrificial cartridge 152, may be configured to represent at least a portion of the purifying capacity (e.g. the useful capacity) of one or more of the air purifying elements 112. Thus the reduced air flow through the sacrificial cartridge 152 may be referred to as being proportionate to the air flow through one or more of the air purifying elements 112. Upon consuming the capacity of the air purifying media in the sacrificial cartridge 152, one or more contaminants may break through the sacrificial cartridge 152 and be measured by the downstream sensor 156. As a result, the calibration of the relative capacity of the sacrificial cartridge 152 relative to the useful capacity of the one or more air purifying elements 112 may provide an indication of the portion of the purifying capacity consumed in one or more of the air purifying elements 112. As used herein, the term "relative capacity" or "relative purifying capacity" takes into account the difference in the size and amount air purifying media through the consideration of the proportional air flow along with the reduced capacity of the sacrificial cartridge relative to the total and/or useful capacity of the air purifying elements 112. In an embodiment, the sacrificial cartridge 152 may be configured to have a purifying capacity of about 50%, about 60%, about 70%, about 80%, about 90%, about 95%, or about 99% of the purifying capacity of one or more of the air purifying elements 112. The purifying capacity of the sacrificial cartridge 152 may be selected based at least in part on considerations including the type of environment in which the breathing apparatus is to be used, the types of contaminants expected to be encountered, and any governmental regulations affecting exposure limits and/or capacity warning thresholds. For example, the NIOSH guidelines provide that a reliable and accurate warning be provided before about 90% of the useful capacity of the air purifying elements 112 is consumed, which may be used to select a relative capacity for the sacrificial cartridge 152 of about 90% or less of the useful capacity of one or more of the air purifying elements 112. In an embodiment, a plurality of sacrificial cartridges 152 having the same or different relative capacities with respect to one or more of the air purifying elements 112 may be used with the ESLI 150.

The sacrificial cartridge 152 may be of a similar configuration as the air purifying elements 112 and/or may contain a similar air purifying media. The use of a similar configuration and/or air purifying media may allow for a reliable indication of the end of the service life of the air purifying elements 112. Any of the of the configurations described herein with respect to the air purifying elements 112 may be used as the configuration of the sacrificial cartridge 152. For example, the sacrificial cartridge 152 may be a filter canister, a cartridge, and/or a patch. Further, any of the air purifying media described herein with respect to the air purifying elements 112 may be used in the sacrificial cartridge 152. For example, the sacrificial cartridge 152 may comprise a particulate filter media such as a high efficiency particulate air (HEPA) filter, an ultra-low penetration air filler (ULPA), or the like. Other suitable air purifying media may include, but are not limited to, those disclosed herein for removing one or more gaseous contaminants (e.g., organic and/or inorganic compounds) including, but not limited to, ion exchange resins, activated carbon, impregnated carbon, alumina and other metal oxides that can remove a vapor of interest by adsorption, treated clays and other minerals comprising acidic solutions such as acetic acid or alkaline solutions such as aqueous sodium hydroxide, molecular sieves (e.g., various zeolites), other inorganic sorbents (e.g., silica), various organic sorbents, metal-organic frameworks (MOFs), and any combinations thereof. The form (e.g., fiber media, particulates, solids, etc.) of the air purifying media present in the sacrificial cartridge 152 may be the same or similar to the form of the air purifying media in the air purifying elements 112.

The sensor 156 may be used to detect the presence of one or more contaminants in the air within the flow apparatus 164 downstream of the sacrificial cartridge 152. Based on the detection of the one or more contaminants, the sensor 156 may be used to determine when the sacrificial cartridge 152 experiences a breakthrough of a contaminant through the sacrificial cartridge 152 (i.e., the time at which the sacrificial cartridge 152 no longer reduces the amount of the contaminant of interest to a predetermined threshold). As described above, a proportionate amount of air is delivered to the sacrificial cartridge 152 as compared to one or more of the air purifying elements 112. When the sensor 156, which is located downstream from the sacrificial cartridge 152, detects the contaminant of interest it may be taken a signal that the capacity of the sacrificial cartridge 152 has been consumed. Since the capacity of the sacrificial cartridge 152 is proportional to a portion of the capacity of one or more of the air purifying elements 112, it can be inferred that the portion of the capacity of one or more of the air purifying elements 112 has also been consumed.

The sensor 156 can be any device that can detect the presence of a specified chemical, component, or family of chemicals or components. Suitable sensors may include, but are not limited to, optical and adsorption type sensors. In an embodiment, the sensor may comprise a metal oxide sensor (MOS) and/or a photoionization detector (PID). The sensor 156 is capable of detecting the specified chemical, component, or family of chemicals or components to a predetermined threshold. In an embodiment, the various specified components can be detected to approximately a parts per million (ppm) level, or in some embodiments, to a parts per billion (ppb) level. Depending on the range of specified components to be detected, a plurality of sensors may be used, where the sensors may each be different and may each detect different types of specified chemicals, components, or families of chemicals or components.

When multiple chemicals are present in the ambient air, the sensor 156 may be selected to detect one or more representative components of the plurality of chemicals. The representative component may be used to indicate that the capacity of the sacrificial cartridge 152 has been consumed with respect to all of the contaminants present in the ambient air. For example, a single organic compound or small group of organic compounds may be detectable by the sensor 156, and the detection of the single organic compound or any member of the small group of organic compounds may be used to indicate that the capacity of the sacrificial cartridge 152 has been consumed with respect to all or a family of organic compounds. Thus, the sensor 156 need not be capable of detecting all of the contaminants that may be present in the air in order to provide a reliable indication of the consumption of the capacity of the sacrificial cartridge 152, and by implication, one or more of the air purifying elements 112.

In the embodiment shown in FIG. 1, the ESLI 150 may be disposed within the housing assembly 104, though in other embodiments discussed below the ESLI 150 may be external or separate from the housing assembly 104. When the ESLI 150 is disposed within the housing assembly 104, the housing assembly 104 may be sized to accommodate the flow apparatus 164, the sensor 156, and/or the secondary blower assembly 154. The power source 124 and the controller 128 may be coupled to the sensor 156 and the secondary blower assembly 154 to provide power and operational control signals to the sensor 156 and/or the secondary blower assembly 154. The flow apparatus 164 may pass through the enclosure 118 of the pump while be substantially sealed to fluid communication with the enclosure 118. Alternatively, the flow apparatus 164 may be in a separate compartment within the housing assembly 104 to further separate the flow apparatus from the enclosure 118. Such separation may protect against the potential contamination of the air in the enclosure 118 by the air in the flow apparatus 164 once a breakthrough of the sacrificial cartridge 152 has occurred.

The secondary blower assembly 154 is coupled in fluid communication with the ESLI inlet 162 and the ESLI outlet 160 to facilitate drawing air through the sacrificial cartridge 152 and past the sensor 156. While FIG. 1 illustrates the sensor 156 upstream of the secondary blower assembly 154, the sensor 156 may be disposed downstream of the secondary blower assembly 154 in some embodiments. The secondary blower assembly 154 may be configured to provide a predetermined air flow that may be varied to maintain a proportional air flow through the sacrificial cartridge 152 relative to the one or more air purifying elements 112. In an embodiment, the secondary blower assembly 154 may be electronically-controlled. The secondary blower assembly 154 generally comprises a blower and a motor to drive the blower. In an embodiment, the secondary blower assembly 154 may comprise any type of blower including, but not limited to, a centrifugal fan, a low profile fan, impeller, rotary air pump, or the like.

In an embodiment, the controller 128 may be coupled to a sensor to monitor the speed of the secondary blower in the secondary blower assembly 154 and control the speed of the motor driving the secondary blower. The controller 128 may then be used to ensure that the flow rate of air through the sacrificial cartridge 152 is at or above a proportionate flow rate as compared to the air purifying elements 112.

In an embodiment, the proportionate flow rate through the sacrificial cartridge 152 as compared to the air purifying elements 112 may be determined from a consideration of the total and/or useful capacity of the one or more of the air purifying elements 112 and the capacity of the sacrificial cartridge 152. Considering a case with n air purifying elements 112 each having a capacity of A, and a total air flow rate through the breathing apparatus of a, the capacity of the air purifying elements 112 may be consumed at a time t(A) for a certain contaminant concentration, $C_{air}$, in the air. Further considering that the sacrificial cartridge 152 may have a selected capacity of B and a desired flow rate through the ESLI 150 of b, the capacity of the sacrificial cartridge 152 may be consumed at a time t(B) for the same contaminant concentration, $C_{air}$, in the air. While the inlet of the air purifying elements 112 are proximate the inlet 158 of the sacrificial cartridge 152, the contaminant concentration in the air may be assumed to be approximately equal. The breakthrough condition of the air purifying elements 112 and the sacrificial cartridge 152 may be expressed as:

$$\left(\frac{a}{n}\right) C_{air} t(A) = A \qquad \text{Eq. 1}$$

$$b C_{air} t(B) = B \qquad \text{Eq. 2}$$

Equations 1 and 2 may be solved for t(A) and t(B) to give:

$$t(A) = \frac{nA}{aC_{air}} \qquad \text{Eq. 3}$$

$$t(B) = \frac{B}{bC_{air}} \qquad \text{Eq. 4}$$

Based on the relative capacity ($Capacity_{rel}$) of the sacrificial cartridge 152 to the useful capacity of an air purifying element 112, the relationship of the breakthrough times may be established and the lower limit of the flow rate through the sacrificial cartridge 152 may be determined as:

$$t(B) \leq Capacity_{rel} t(A) \qquad \text{Eq. 5}$$

Where t(A) and t(B) may be substituted using equations 3 and 4 to provide:

$$\frac{B}{bC_{air}} \leq \frac{Capacity_{rel} nA}{aC_{air}} \qquad \text{Eq. 6}$$

$$b \geq \frac{aB}{Capacity_{rel} nA} \qquad \text{Eq. 7}$$

The flow rate through the ESLI 150 of b may be calculated using equation 7 while also taking into account the uncertainties in the capacity of the sacrificial cartridge 152, B, the total and/or useful capacity of the air purifying elements 112, A, the measurement of the air flow rate a through the air purifying elements 112, and the assumption that the air flow equally partitions between the n air purifying elements 112. While the capacity of the sacrificial cartridge 152 may be selected to be small relative to the capacity of the air purifying elements 112, a practical limit is imposed due to the uncertainties in the values of A, B, and a. In order to predict the breakthrough with a desired degree of safety, the value of $Capacity_{rel}$ may be reduced as the uncertainties in the values of A, B, and a increase. In an embodiment, the $Capacity_{rel}$ may be about 90% (i.e., about 0.9) to represent the ratio of the capacity of the sacrificial cartridge 152, B, to the useful capacity of the air purifying elements 112, A.

The controller 128 may be used to maintain the proportionate flow rate through the sacrificial cartridge 152 based on the measured flow rate through the air purifying elements 112, the capacities of both the sacrificial cartridge 152 and the air purifying elements 112, and the predetermined relative capacity of the sacrificial cartridge 152 with respect to the air purifying elements 112. In an embodiment, the controller 128 may be connected to a speed sensor that senses that rotational speed of the shaft of the secondary motor, compares the sensed speed to a correlation between the shaft speed and the secondary blower output, and adjusts the power to the secondary motor so that the sensed speed corresponds to at least the proportional flow rate through the sacrificial cartridge 152. This type of control may allow for a change in the output of the secondary blower assembly 154 in response to a change in the flow rate through the blower assembly 126. For example, the deposition of particulate matter in a particulate filter in the air purifying elements 112 may result in a decrease in the flow rate through the breathing apparatus 100. The controller 128 may detect this flow rate decrease and adjust the secondary blower assembly 154 flow rate to be proportional, thereby allowing a more accurate determination of the time to breakthrough of the sacrificial cartridge 152. To allow this type of control, the controller 128 may have a power supply circuit that is connected to the power source 124 and the secondary motor to control the current supplied to the secondary motor.

In use, the ESLI 150 may be independently controlled through the use of a power switch or other activation mechanism and/or through an activation signal from the controller 128 associated with the breathing apparatus 100. When activated either independently or through the controller 128 in the housing assembly 104, the secondary blower assembly 154 may activate to produce a proportionate flow rate through the sacrificial cartridge 152 relative to the air purifying elements 112. The air may pass from the sacrificial cartridge 152 past the sensor 156 and the secondary blower assembly 154 to exhaust through the ESLI outlet 160 to the ambient environment. The ESLI 150 may then function to detect any contaminants in the air passing over the sensor 156 until a breakthrough is detected. Upon the detection of a breakthrough, an indication such as an output signal including, but not limited to, an audible signal, a visual signal, and/or a tactile signal (e.g., a vibration) may be generated to indicate the breakthrough of the sacrificial cartridge 152. Alternatively or in addition to the indication, a sensor output may be generated and received by the controller 128 for use with an optional user interface or indicator device 166 associated with the breathing apparatus 100.

The indication of the breakthrough may be taken as a signal that the selected portion of the capacity of the one or more air purifying elements 112 has been consumed. In an embodiment, the secondary blower assembly 154 and/or the sensor 156 may be shut off once a breakthrough has been detected to save power. The user may then proceed to replace one or more of the air purifying elements 112 during or after use of the breathing apparatus 100 is discontinued. The sacrificial cartridge 152 may be replaced with a new sacrificial cartridge 152 at approximately the same time that the air purifying elements 112 are replaced to provide a further ESLI indication for the newly replaced air purifying elements 112. This process may be repeated any number of times to provide a reusable ESLI 150. Alternatively, the breathing apparatus 100 and ESLI 150 may comprise a disposable or single use device, and the detection of the breakthrough of the sacrificial cartridge 152 may be taken as an indication that the device should be discarded and/or replaced.

Figure 2:
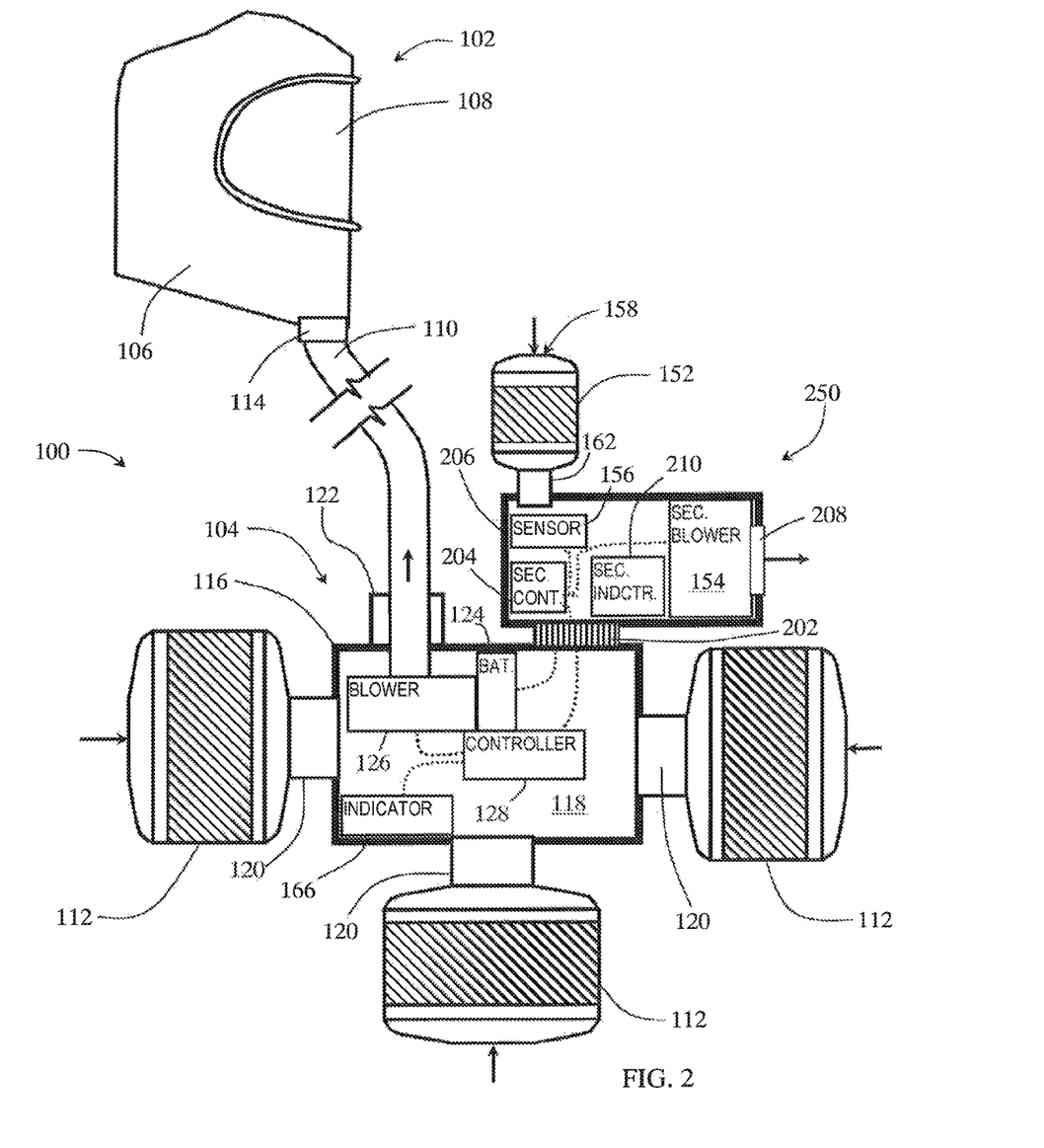
FIG. 2 schematically illustrates another breathing apparatus and service life indicator according to an embodiment.

FIG. 2 schematically illustrates another embodiment of the breathing apparatus 100 and the ESLI 250. This embodiment is similar to the embodiment illustrated in FIG. 1 except that the ESLI 250 is externally coupled to the breathing apparatus 100. The components of the ESLI 250 are generally the same as those discussed above with respect to the ESLI 150 of FIG. 1, and the same or similar components will not be discussed with respect to FIG. 2 for clarity. The embodiment of the ESLI 250 illustrated in FIG. 2 may additionally have a communication interface 202, an optional secondary controller 204, and a separate secondary housing assembly 206 as compared to the ESLI of FIG. 1.

The secondary housing assembly 206 comprises the ESLI inlet 162 with a corresponding sacrificial cartridge 152 coupled thereto and at least one exhaust port 208. The secondary housing assembly 206 may be substantially sealed so that the ESLI inlet 162 provides the only means for air to enter the secondary housing assembly 206 prior to passing by the sensor 156 and the secondary blower assembly 154 before being exhausted through the ESLI outlet 208 to the ambient environment.

The communication interface 202 may comprise any number of electrical connections for transmitting power and electrical signals between the ESLI 250 and the breathing apparatus 100. Various connectors and interfaces comprising multiple electrical connections such as pin connectors are known for electrically coupling components. In an embodiment, one or more of the connections may be used to provide power from the power source 124 to the ESLI 250 to operate the secondary blower assembly 154, the sensor 156, and/or the optional secondary controller 204. In addition, one or more of the connections may be used to exchange signals between the secondary blower assembly 154, the sensor 156, and/or the optional secondary controller 204 in the ESLI 250 and the controller 128 in the breathing apparatus 100. For example, the air flow rate within the breathing apparatus 100 may be communicated to the secondary blower assembly 154 in the ESLI 250 through the communication interface 202.

A portion of the communication interface 202 may be disposed in and/or on the housing assembly 104 of the breathing apparatus 100, and a corresponding interface portion may be disposed in and/or on the secondary housing assembly 206 associated with the ESLI 250. The physical coupling of the breathing apparatus 100 and the ESLI 250 about the communication interface 202 may result in the inlet of the sacrificial cartridge 152 being disposed in proximity of the inlet of one or more of the air purifying elements 112. While illustrated as comprising a direct physical coupling, it should be understood that additional coupling elements such as wired connectors and/or cables may also be used. For example, a cable comprising suitable connector ends may be used to couple the breathing apparatus 100 to the ESLI 250. When an additional coupling component is used, the inlet of the sacrificial cartridge 152 may be disposed within the proximity of the inlet of one or more of the air purifying elements 112. In an embodiment, the inlet of the sacrificial cartridge 152 may be disposed within about 10 feet, about 8 feet, about 6 feet, about 4 feet, about 2 feet, or about 1 foot of the inlet of one or more of the air purifying elements 112.

An optional secondary controller 204 may be used to control one or more elements of the ESLI 250. Like the controller 128, the secondary controller 204 may comprise one or more processors, various circuits, an optional memory, and various electrical couplings linking the secondary controller 204 with the controlled components to facilitate communication and control of the secondary blower assembly 154, the sensor 156, the communication interface 202, and any output devices associated with the ESLI 250 that are used to indicate a detected breakthrough of the sacrificial cartridge 152. In an embodiment, the secondary controller 204 may be electrically coupled to a plurality of sensors mounted within the secondary housing 206 including, but not limited to, a speed sensor to detect the rotational speed of the secondary blower associated with the secondary blower assembly 154, a pressure sensor to detect a low air flow or leak, and a voltage sensor to determine proper operation of the electrical components. The secondary controller 204 may comprise a power switch to initiate operation of the ESLI 250. An optional secondary user interface or secondary indicator device 210 may also be associated with the ESLI 250 to allow a user to provide inputs (e.g., setting the predetermined thresholds) and control various operations of the ESLI 250 separate from the controller 128 associated with the breathing apparatus 100. For example, the optional secondary user interface or secondary indicator device 210 may present an audible, visual, and/or tactile alarm on the indicator device 210 in response to receiving an indication of a breakthrough of the sacrificial cartridge 152 as detected by the sensor 156.

The secondary controller 204 may be used to maintain the proportionate flow rate through the sacrificial cartridge 152 based on a signal received from the controller 128 indicating the measured flow rate through the air purifying elements 112, the capacities of both the sacrificial cartridge 152 and the air purifying elements 112, and the predetermined relative capacity of the sacrificial cartridge 152 with respect to the air purifying elements 112. In an embodiment, the secondary controller 204 may be connected to a speed sensor that senses that rotational speed of the shaft of the secondary blower, compares the sensed speed to a correlation between the shaft speed and the secondary blower output, and adjusts the power to the secondary motor so that the sensed speed corresponds to at least the proportional flow rate through the sacrificial cartridge 152. This type of control may allow for a change in the output of the secondary blower assembly 154 in response to a change in the flow rate through the blower assembly 126. For example, the deposition of particulate matter in a particulate filter in the air purifying elements 112 may result in a decrease in the flow rate through the breathing apparatus 100. The controller 128 may detect this flow rate decrease and send a signal indicating the flow rate decrease through the communication interface 202 to the secondary controller 204. The secondary controller 204 may then adjust the secondary blower assembly 154 flow rate to be proportional, thereby allowing a more accurate determination of the time to breakthrough of the sacrificial cartridge 152. To allow this type of control, the secondary controller 204 may have a power supply circuit that is connected to the power source 124 through the communication interface 202 and the secondary motor to control the current supplied to the secondary motor.

In use, the ESLI 250 shown in FIG. 2 may operate in a similar manner to the ESLI 150 shown in FIG. 1. The ESLI 250 may be coupled to the breathing apparatus 100 through the communication interface 202 to provide signal communication and power to the ESLI 250. In an embodiment, the ESLI 250 may be independently controlled through the use of a power switch or other activation mechanism, through an activation signal from the controller 128 and/or the secondary controller 204, and/or upon the coupling of the ESLI 250 and the breathing apparatus 100. Once activated, the secondary blower assembly 154 may produce a proportionate flow rate through the sacrificial cartridge 152 relative to the air purifying elements 112. The air may pass from the sacrificial cartridge 152 past the sensor 156 and the secondary blower assembly 154 to exhaust through the ESLI outlet 208 to the ambient environment. The ESLI 250 may then function to detect any contaminants in the air passing over the sensor 156 until a breakthrough is detected. Upon the detection of a breakthrough, an indication such as an output signal including, but not limited to, an audible signal, a visual signal, and/or a tactile signal may be generated to indicate the breakthrough of the sacrificial cartridge 152. Alternatively or in addition to the indication, a sensor output may be generated and received by the controller 128 for use with an optional user interface or indicator device 166 and/or the secondary controller 204 for use with the optional secondary user interface or secondary indicator device 210.

The indication of the breakthrough may be taken as a signal that the selected portion of the capacity of the one or more air purifying elements 112 has been consumed. In an embodiment, the secondary blower assembly 154 and/or the sensor 156 may be shut off once a breakthrough has been detected to save power. Alternatively, the ESLI 250 may be shut off and/or the ESLI 250 and the breathing apparatus 100 may be decoupled until one or more of the air purifying elements 112 and the sacrificial cartridge is replaced in order to save power from the power source 124. The user may then proceed to replace one or more of the air purifying elements 112 during or after use of the breathing apparatus 100 is discontinued. The sacrificial cartridge 152 may be replaced with a new sacrificial cartridge 152 at approximately the same time that the air purifying elements 112 are replaced to provide a further ESLI indication for the newly replaced air purifying elements 112. This process may be repeated any number of times to provide a reusable ESLI 250. Alternatively, the breathing apparatus 100 and ESLI 250 may comprise a disposable or single use device, and the detection of the breakthrough of the sacrificial cartridge 152 may be taken as an indication that the device should be discarded and/or replaced.

Figure 3:
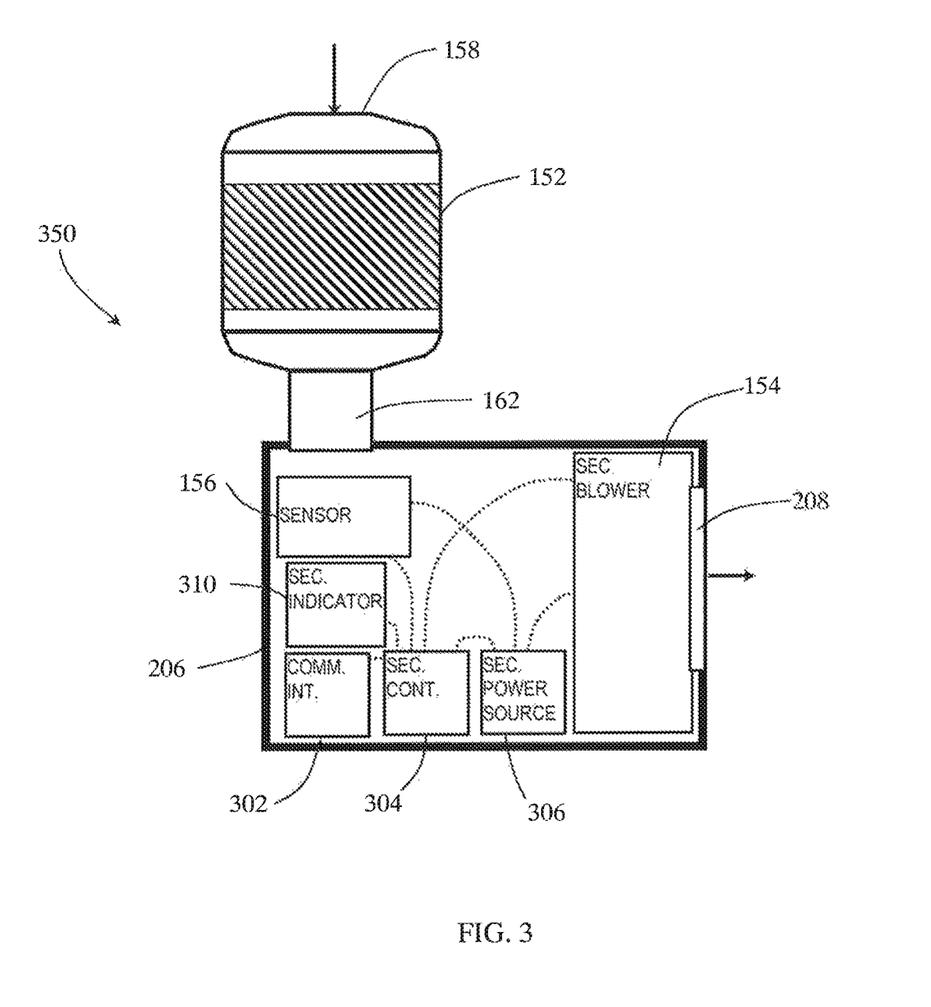
FIG. 3 schematically illustrates still another service life indicator according to an embodiment.

FIG. 3 schematically illustrates another embodiment of the ESLI 350. This embodiment is similar to the embodiment illustrated in FIG. 1 and FIG. 2 except that the ESLI 350 comprises a stand alone module. The components of the ESLI 350 are generally the same as those discussed above with respect to the ESLI 150 of FIG. 1 and the ESLI 250 of FIG. 2, and the same or similar components will not be discussed with respect to FIG. 3 for clarity. The embodiment of the ESLI 350 illustrated in FIG. 3 may also comprise a communication interface 302, a secondary controller 304, a secondary power source 306, and a separate secondary housing assembly 206 as compared to the ESLI 150 of FIG. 1 and the ESLI 250 of FIG. 2. The secondary housing assembly 206 may be the same as the secondary housing assembly 206 described above.

As a stand alone module, the ESLI 350 may not be electrically or physically coupled to a breathing apparatus. A secondary power source 306 may be associated with the secondary housing assembly 206 to provide power to the sensor 156, the secondary blower assembly 154, the communication interface 302, and the secondary controller 304. The secondary power source 306 may comprise a source of electrical power and may include a battery assembly and/or a power supply coupled to an external source of electrical power. Alternatively, the secondary housing assembly 206 may comprise an inverter coupled to a battery assembly to allow the components to be powered by alternating current. The secondary power source 306 may comprise any of the battery types, connection types, or power source types discussed with respect to the power source 124.

The ESLI 350 may comprise a communication interface 302 for sending and/or receiving signals such as control signals, sensor outputs, sensor 156 readings, etc. In an embodiment, one or more breathing apparatuses may also comprise a similar communication interface to provide for communications between the one or more breathing apparatuses and the ESLI 350. The communication interface 302 may comprise wired and/or wireless communication pathways. For example, one or more communication cables may be used to couple the ESLI 350 and a breathing apparatus (e.g., breathing apparatus 100 shown in FIG. 1 and FIG. 2). In an embodiment, the communication interface 302 may comprise one or more network connectivity devices such as modems, modem banks, Ethernet cards, universal serial bus (USB) interface cards, serial interfaces, token ring cards, fiber distributed data interface (FDDI) cards, wireless local area network (WLAN) cards, and other well-known network devices. These network connectivity devices may enable the ESLI 350 to communicate with a corresponding communication interface associated with the breathing apparatus, the Internet, and/or one or more intranets. With such a network connection, it is contemplated that the ESLI 350 or a processor operatively coupled to the breathing apparatus 100, might receive information from the network and/or output information to the network in the course of operating to detect a breakthrough of the sacrificial cartridge 152. Alternatively, a wireless communication device utilizing a wireless communication protocol such as WiFi, BlueTooth, code division multiple access (CDMA), global system for mobile communications (GSM), long-term evolution (LTE), worldwide interoperability for microwave access (WiMAX), and/or other air interface protocols may be used to couple the ESLI 350 to the breathing apparatus. An antenna or other wireless transmitter may be coupled to the ESLI 350 and/or the breathing apparatus for use in sending and/or receiving one or more communication signals. For example, the sensor outputs may be transmitted from the ESLI 350 to the breathing apparatus to allow an indication of a breakthrough of the sacrificial cartridge 152 to be displayed on the optional user interface or indicator device associated with the breathing apparatus. As another example, the blower assembly 126 blower speed may be received by the ESLI 350 for use in controlling the secondary blower assembly 154 blower speed to maintain at least a proportional air flow through the sacrificial cartridge 152.

While the communication interface 302 may provide for wired or wireless communication, the inlet of the sacrificial cartridge 152 may still be disposed within the proximity of the inlet of one or more of the air purifying elements 112 in order to ensure that approximately the same contaminant concentration is being sampled by both the sacrificial cartridge 152 and the one or more air purifying elements 112. In an embodiment, the inlet of the sacrificial cartridge 152 may be disposed within about 10 feet, about 8 feet, about 6 feet, about 4 feet, about 2 feet, or about 1 foot of the inlet of one or more of the air purifying elements 112.

The secondary controller 304 may be used to control one or more elements of the ESLI 350. Like the controller 128, the secondary controller 204 may comprise one or more processors, various circuits, an optional memory, and various electrical couplings linking the secondary controller 304 with the controlled components and the communication interface 302 to facilitate control of the secondary blower assembly 154, the sensor 156, the communication interface 302, and/or any output devices associated with the ESLI 350 that are used to indicate a detected breakthrough of the sacrificial cartridge 152. The secondary controller 304 may comprise a plurality of sensors mounted with the secondary housing and an optional secondary user interface or secondary indicator device as described in more detail with respect to the secondary controller 204 illustrated in FIG. 2. Similarly, the secondary controller 304 may be used to maintain the proportionate flow rate through the sacrificial cartridge 152 based on a signal received from the controller 128 through the communication interface 302 in the same manner as described herein with respect to the secondary controller 204 illustrated in FIG. 2.

In use, the ESLI 350 shown in FIG. 3 may operate in a similar manner to the ESLI shown in FIG. 1 and FIG. 2. The ESLI 350 may be disposed in proximity to the air purifying elements coupled to the breathing apparatus. In an embodiment, the ESLI 350 may be independently controlled through the use of a power switch or other activation mechanism and/or through an activation signal from the controller 128 and/or the secondary controller 304. In an embodiment, communication may be established between a communication interface associated with the breathing apparatus and a communication interface 302 associated with the ESLI 350 once the breathing apparatus and the ESLI 350 are active. Once the ESLI 350 is activated and communication has been established with the breathing apparatus, the secondary blower assembly 154 may activate to produce a proportionate flow rate through the sacrificial cartridge 152 relative to the air purifying elements 112. The air may pass from the sacrificial cartridge 152 past the sensor 156 and the secondary blower assembly 154 to exhaust through the ESLI outlet 208 to the ambient environment. The ESLI 350 may then function to detect any contaminants in the air passing over the sensor 156 until a breakthrough is detected. Upon the detection of a breakthrough, an indication such as an output signal including, but not limited to, an audible signal, a visual signal, and/or a tactile signal may be generated to indicate the breakthrough of the sacrificial cartridge 152. The indication may be displayed or presented on the optional secondary user interface or secondary indicator device 310 and/or the output signal may be transmitted to the breathing apparatus through the communication interface 302 for display on the optional user interface associated with the breathing apparatus.

The indication of the breakthrough may be taken as a signal that the selected portion of the capacity of the one or more air purifying elements 112 has been consumed. In an embodiment, the secondary blower assembly 154 and/or the sensor 156 may be shut off once a breakthrough has been detected to save power. The user may then proceed to replace one or more of the air purifying elements 112 during or after use of the breathing apparatus is discontinued. The sacrificial cartridge 152 may be replaced with a new sacrificial cartridge 152 at approximately the same time that the air purifying elements 112 are replaced to provide a further ESLI indication for the newly replaced air purifying elements 112. This process may be repeated any number of times to provide a reusable ESLI 350. Alternatively, the breathing apparatus 100 and ESLI 350 may comprise a disposable or single use device, and the detection of the breakthrough of the sacrificial cartridge 152 may be taken as an indication that the device should be discarded and/or replaced.

While described above with reference to the specific embodiments illustrated in FIGS. 1-3, the service life indicator described herein may be used with a system comprising a breathing apparatus in a broad sense to purify a first air stream using a breathing apparatus comprising an air purifying element to produce a purified first stream; supply the purified first air stream to a user; pass a second air stream through a sacrificial cartridge to produce a third stream; exhaust the third stream to an ambient environment; and detect a contaminant concentration above a predetermined threshold in the third stream. The system may also be used to provide an indication in response to detecting the contaminant concentration above the predetermined threshold in the third stream and replace the air purifying element and the sacrificial cartridge in response to detecting the contaminant concentration above the predetermined threshold in the third stream. All of these steps may be repeated a plurality of times to allow for the re-use of the service life indicator.

While an exemplary embodiment of the breathing apparatus 100 has been described in the context of a PAPR, the methods and apparatus described herein are not limited to being a PAPR as the present disclosure may be used with other types of breathing apparatuses comprising filter elements. For example, the present invention may be used with respirators used for air filtration, those that provide a positive pressure supply of air from a pressure vessel, or any combination thereof.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein. Other steps may be provided in the methods described herein, or steps may be eliminated, and other components may be added to, or removed from, the systems described herein. Other embodiments may be within the scope of the following claims.

What is claimed is:

1. A respirator service life indication system comprising:
a breathing apparatus comprising an inlet port, and outlet port, and an air purifying element coupled to the inlet port for the breathing apparatus; and
a service life indicator arranged in a parallel flow configuration with the breathing apparatus such that the service life indicator has a separate inlet and outlet from the inlet port and the outlet port of the breathing apparatus so air entering the service life indicator through the inlet separate and apart from the inlet port of the breathing apparatus is exhausted to ambient environment through the outlet separate and apart from the outlet port of the breathing apparatus and does not contact or mix with air passing through the breathing apparatus, wherein the service life indicator comprises:
a sacrificial cartridge, and
a sensor disposed downstream of the sacrificial cartridge and configured to detect a contaminant concentration above a predetermined threshold in an gas stream passing through the sacrificial cartridge.

2. The system of claim 1, wherein the air purifying element and the sacrificial cartridge each comprise a purifying media configured to remove one or more particulate materials from the gas stream passing through the purifying media.

3. The system of claim 2, wherein the purifying media comprises a high efficiency particulate air filter or an ultra-low penetration air filter (ULPA).

4. The system of claim 1, wherein the air purifying element and the sacrificial cartridge each comprise a purifying media configured to remove a gaseous contaminant from the gas stream passing through the purifying media.

5. The system of claim 4, wherein the gaseous contaminant comprises a volatile organic compound.

6. The system of claim 4, wherein the purifying media comprises a sorbent media selected from the group consisting of: an ion exchange resin, activated carbon, impregnated carbon, a metal oxide, a treated clay, a molecular sieve, silica, a metal-organic framework, and any combination thereof.

7. The system of claim 1, wherein an inlet of the sacrificial cartridge is located within about 10 feet of an inlet of the air purifying element.

8. The system of claim 1, wherein the breathing apparatus further comprises a housing assembly, and wherein the sensor is disposed within the housing assembly.

9. The system of claim 1, wherein the service life indicator is coupled to the breathing apparatus by a communication interface.

10. The system of claim 9, wherein the communication interface is configured to provide one or more wireless communication pathways between the service life indicator and the breathing apparatus.

11. The system of claim 1, wherein the breathing apparatus further comprises a valve operable to seal the inlet port when the air purifying element is not coupled thereto.

12. The system of claim 1, wherein the breathing apparatus further comprises a second inlet port with a second air purifying element coupled thereto.

13. A powered air-purifying respirator service life indication system comprising:
a powered air-purifying respirator comprising:
one or more air purifying elements, and
a blower assembly configured to draw a first air stream from an ambient environment through an inlet, pass the first air stream through the one or more air purifying elements, and pass the first air stream to a mask;
a service life indicator comprising:
a sacrificial cartridge,
a sensor disposed downstream of the sacrificial cartridge, and
a secondary blower assembly configured to draw a second air stream from the ambient environment through an inlet separate from the inlet of the respirator, pass the second air stream through the sacrificial cartridge and past the sensor, and pass the second air stream back to the ambient environment through an outlet separate from an outlet of the blower assembly; and
an indicator device configured to present an indication from the sensor in response to the detection of a contaminant concentration above a predetermined threshold in the second air stream.

14. The system of claim 13, wherein the one or more air purifying elements are coupled to the powered air-purifying respirator by a first connection mechanism, wherein the sacrificial cartridge is coupled to the service life indicator by a second connection mechanism, and wherein the first connection mechanism and the second connection mechanism are different or differently sized.

15. The system of claim 13, wherein the powered air-purifying respirator further comprises a controller coupled to the blower assembly of the powered air-purifying respirator, wherein the controller is configured to determine a flow rate of the first air stream, and wherein a flow rate of the second air stream is based on the flow rate of the first air stream determined by the controller.

16. The system of claim 13, wherein the second air stream has a proportional air flow rate to a flow rate of the first air stream.

17. The system of claim 13, wherein the sacrificial cartridge is configured to have a relative purifying capacity of about 90% or less of a purifying capacity of the air purifying element.

18. The system of claim 13, wherein a flow rate of the second air stream is related to a flow rate of the first air stream through the equation:

$$b \geq \frac{aB}{Capacity_{rel} nA}$$

wherein, b is the flow rate of the second air stream, a is the flow rate of the first air stream, B is a purifying capacity of the sacrificial cartridge, A is a purifying capacity of the air purifying element, n is a number of the one or more air purifying elements, and $Capacity_{rel}$ is a ratio of the purifying capacity of the sacrificial cartridge as compared to the purifying capacity of one of the air purifying elements.

19. A system comprising:
a breathing apparatus comprising:
a housing assembly comprising a housing having a plurality of inlet ports with one air purifying element removably coupled to each inlet port by a connection mechanism, and
a service life indicator arranged in parallel flow configuration with the breathing apparatus such that the service life indicator has a separate inlet and outlet from the inlet port and the outlet port of the breathing apparatus so air entering the service life indicator through the inlet separate and apart from the inlet port of the breathing apparatus is exhausted to ambient environment through the outlet separate and apart from the outlet port of the breathing apparatus and does not contact or mix with air passing through the breathing apparatus, wherein the service life indicator comprises:
a sacrificial cartridge, and
a sensor disposed downstream of the sacrificial cartridge and configured to detect a contaminant concentration above a predetermined threshold in a gas stream passing through the sacrificial cartridge;
wherein the housing is sized to be portably carried by a user; and
wherein the plurality of air purifying elements are removably coupled to the inlet ports so as to be located external to the housing.

20. The system of claim 19, wherein the housing assembly further comprises:
a first blower for drawing air into the air purifying elements, through the plurality of inlet ports, and through the outlet port to a mask;
a service life indicator inlet operable for the sacrificial cartridge to be removably coupled to the housing;
a secondary blower for the service life indicator; and
a flow apparatus providing fluid communication from the service life indicator inlet to the secondary blower, and through to a service life indicator outlet in the housing;
wherein the sacrificial cartridge removably couples by connection mechanism to the exterior of the housing to be located external to the housing;
wherein the secondary blower provides air flow through the service life indicator by drawing air into the sacrificial cartridge, through the service life indicator inlet, and through the flow apparatus;
wherein the service life indicator is sealed to prevent mixing of air passing through the service life indicator with air passing to the mask;
wherein the service life indicator and the breathing apparatus have separate inlets and outlets on the housing; and
wherein the connection mechanism for the sacrificial cartridge is different or differently sized than the connection mechanisms for the air purifying elements.

* * * * *